(12) United States Patent
Henckel et al.

(10) Patent No.: US 7,785,820 B2
(45) Date of Patent: Aug. 31, 2010

(54) METHOD FOR AUTOMATICALLY DETERMINING THE ENDOGENOUS THROMBIN POTENTIAL

(75) Inventors: Thilo Henckel, Wetter (DE); Andreas Weyl, Münchhausen (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 874 days.

(21) Appl. No.: 11/294,382

(22) Filed: Dec. 6, 2005

(65) Prior Publication Data

US 2006/0121617 A1 Jun. 8, 2006

(30) Foreign Application Priority Data

Dec. 7, 2004 (DE) .................... 10 2004 059 055

(51) Int. Cl.
*C12Q 1/56* (2006.01)
*G01N 33/86* (2006.01)
(52) U.S. Cl. .................. 435/13; 436/34; 436/69; 436/70; 702/19
(58) Field of Classification Search .............. 436/34, 436/69, 70; 435/13; 702/19
See application file for complete search history.

(56) References Cited

U.S. PATENT DOCUMENTS 6,321,164 B1 * 11/2001 Braun et al. .................. 702/22

FOREIGN PATENT DOCUMENTS

| EP | 0 420 332 B1 | 4/1995 |
|---|---|---|
| EP | 0 456 152 B1 | 11/1998 |
| EP | 0 802 986 B1 | 9/2001 |
| WO | WO03/079149 | 9/2003 |
| WO | WO2004/016807 A1 | 2/2004 |

OTHER PUBLICATIONS

H.C. Hemker et al., "Continuous Registration of Thrombin Generation in Plasma, Its Use for the Determination of the Thrombin Potential," *Thrombosis and Haemostasis* 70(4): 617-624 (1993).
S. Wielders et al., "The Routine Determination of the Endogenous Thrombin Potential, First Results in Different Forms of Hyper- and Hypocoagulability," *Thrombosis and Haemostasis*, 77(4): 629-636 (1997).
H. Kessels et al., "Analysis of Thrombin Generation in Plasma," *Comput. Biol. Med*, 24(4): 277-288 (1994).
H. C. Hemker et al., "Thrombin Generation in Plasma: Its Assessment Via the Endogenous Thrombin Potential," *Thrombosis and Haemostasis*, 74(1) 134-138 (1995).
H.C. Hemker et al., "A computer-assisted method to obtain the prothrombin activation velocity in whole plasma independent of thrombin decay processes," *Thrombosis and Haemostasis* 56(1): 9-17 (1986).

* cited by examiner

*Primary Examiner*—Jill Warden
*Assistant Examiner*—Dean Kwak
(74) *Attorney, Agent, or Firm*—Finnegan, Henderson, Farabow, Garrett & Dunner, L.L.P.

(57) ABSTRACT

The present invention relates to a method for automatically determining the endogenous thrombin potential of a blood or plasma sample.

16 Claims, 4 Drawing Sheets

METHOD FOR AUTOMATICALLY DETERMINING THE ENDOGENOUS THROMBIN POTENTIAL

Figure 1:
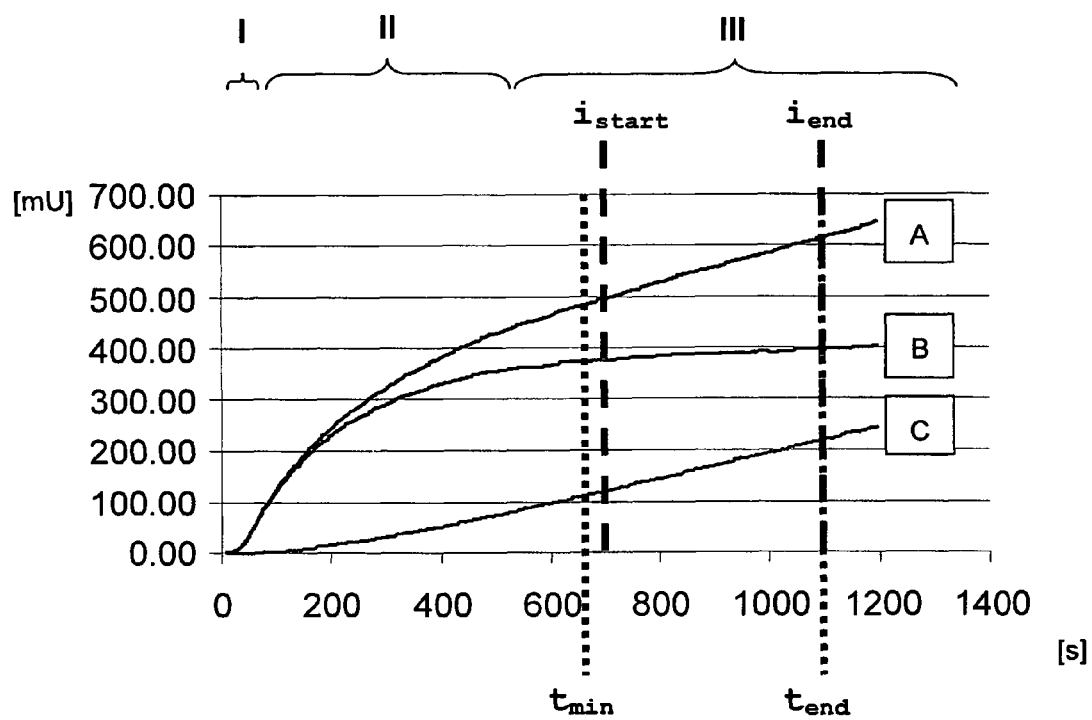

The present invention relates to a method for automatically determining the endogenous thrombin potential of a blood or plasma sample.

Hemostasis is regulated by the interaction of different activators, inhibitors and positive and negative feedback mechanisms. Defects in this structural organization can lead to an imbalance in the hemostasis system and result either in a hemorrhage or in a thrombosis.

Thrombin, a serine protease, is the central enzyme of plasma blood coagulation with its main function being the induction of fibrin polymerization and thus clot formation. As the need arises, the formation of thrombin is initiated by activation of the enzymically inactive precursor molecule prothrombin. In order to limit the coagulation process locally and chronologically when an injury occurs, the coagulation is throttled promptly, inter alia by the free thrombin being completed by inhibitory factors such as antithrombin or $\alpha_2$-macroglobulin ($\alpha_2$M) and thereby inactivated. Disturbances in the processes which regulate thrombin formation or inhibition can lead to hypercoagulatory or hypocoagulatory states and thus to pathological disturbances in coagulation. Recording the formation and inhibition of thrombin is therefore immensely valuable in providing information with regard to the particular coagulation state.

The ability (potential) which is inherent (endogenous) in a sample, in the case of plasma samples the ability which is inherent in the plasma, to form and inhibit enzymically active, free thrombin is also termed the endogenous thrombin potential (ETP). Since all the biological components which are present in a material under investigation and which are able to influence the formation and inhibition of thrombin determine the individual thrombin potential of a sample, the ETP determination is suitable for use both as a global test, which can be used for detecting several components of the hemostasis system, and for monitoring therapeutic measures.

A parameter which is preferably determined for quantifying the endogenous thrombin potential, and which is also referred to as "endogenous thrombin potential" in the literature, is the time/concentration integral or the area under the thrombin formation curve [see EP 0 420 332-B1, EP 0 802 986-B1 and Hemker et al. (1993) Thromb. Haemostasis 70: 617-624]. This parameter is a measure of the quantity and activity of the endogenous thrombin which has been present, since a time t=0, in a sample of coagulating blood or plasma.

In order to determine the ETP, the turnover kinetics of a thrombin substrate are measured, by the release of a measurable indicator, in a sample of coagulation-capable blood or plasma. Since the thrombin substrate concentration is adjusted such that the substrate cannot be completely consumed during the course of the reaction, the quantity of indicator released is ideally proportional to the enzymic activity of the thrombin which is formed during the course of the coagulation reaction.

However, it is known that the currently available thrombin substrates, which have a molecular size of less than 8 kD, also measure the physiologically irrelevant activity of the $\alpha_2$-macroglobulin/thrombin complex ($\alpha_2$MT) in addition to the physiologically relevant activity of the free thrombin. Measuring the quantity of indicator which is released over time results in a reaction kinetics which, despite progressive, and finally complete, inhibition of the free thrombin, does not reach a plateau phase but, instead, continues to rise.

In order to derive the physiologically relevant thrombin kinetics T(t) when taking the measured overall reaction kinetics as the starting point, it is necessary, as is known, to determine the fraction represented by the activity of the $\alpha_2$MT complex of $\alpha_2$MT(t), and subtract this from the total kinetics K(t):

$$T(t) = K(t) - \alpha_2 MT(t) \qquad (1)$$

The quantity of $\alpha_2$MT complex is directly dependent on the quantity of free thrombin. Free thrombin is first of all formed from the enzymically inactive precursor molecule prothrombin, with the free thrombin then immediately being bound by $\alpha_2$-macroglobulin, resulting in the formation of the relatively stable $\alpha_2$MT complex. Since, therefore, the concentration of $\alpha_2$MT complex changes proportionally to the thrombin concentration during the course of the reaction, the mathematical relationship between the thrombin kinetics T(t) and the kinetics of the $\alpha_2$MT complex $\alpha_2$MT(t), has been described as a differential equation [Hemker et al. (1993) Thromb. Haemostasis 70: 617-624]:

$$\frac{\partial [\alpha_2 MT(t)]}{\partial t} = C \cdot T(t) \qquad (2)$$

in which $\partial$ is the partial derivative, $\alpha_2$MT(t) is the concentration of $\alpha_2$-macroglobulin/thrombin complex at time t, T(t) is the concentration of thrombin at time t, and C is the constant for the binding of thrombin to $\alpha_2$M.

Previously known evaluation methods for determining the endogenous thrombin potential or the concentration of free thrombin [Hemker et al. (1993) Throm. Haemostasis 70: 617-624; WO 2004/016807-A1] describe very complex approaches for solving this differential equation (2). The known methods determine the kinetics of the $\alpha_2$-macroglobulin/thrombin complex by first of all forming the 1st derivative of the overall reaction kinetics. The averagings which are required as a consequence of this analytical procedure can lead to inaccuracies in sum. Complex optimization methods, e.g. the modified Newton method from the "Microsoft EXCEL Solver" software program, whose specification is for the most part unknown to the user, and which does not always reach a result, either, are specified for determining the constant C for the binding of thrombin to $\alpha_2$-macroglobulin. What is more, a number of enzyme-kinetic parameters, such as the Michaelis constants of specific substrates, are taken into account in order to be able to draw conclusions with regard to the quantity of free thrombin based on the quantity of reactive substrate. These substrate-specific parameters either have to be known from the literature or have to be determined, for the substrate employed, in preliminary experiments.

Implementing the previously known methods for determining the endogenous thrombin potential in analyzers which are used in a coagulation laboratory is limited insofar as a high data storage capacity is required, due to the complexity of the previously known methods, and a relatively long calculation time results. For reasons of capacity, long processing times are particularly disadvantageous in the case of diagnostic laboratories, which have to cope with a high sample throughput.

The present invention was consequently based on the object of making available a simplified method which enables the endogenous thrombin potential to be determined rapidly and reliably on analytical equipment which is customary in coagulation diagnosis.

This object is achieved by providing the methods and subject matter according to the invention which are described in the claims.

The present method for determining the endogenous thrombin potential (ETP) of a sample comprises
1. the measurement, which is known to the skilled person, of the turnover kinetics of a thrombin substrate as a function of time, and
2. the determination, according to the invention, of a raw ETP value which enables the endogenous thrombin potential of a sample to be quantified.

The measurement, which is necessary for determining the endogenous thrombin potential, of the turnover kinetics of a thrombin substrate requires that the sample to be investigated be treated with a thrombin substrate, that thrombin formation be induced, e.g. by adding a thrombin formation activator, and that a physical or chemical property of the converted thrombin substrate be measured as a function of time.

Blood or plasma, of human or animal origin is, for example, suitable for use as sample material. Platelet-poor or platelet-rich plasma which can be treated with EDTA and/or citrate is particularly well suited for this purpose.

Suitable thrombin substrates are, for example, oligopeptides which are composed of a part which encompasses a specific sequence for recognition by thrombin and of a leaving signal group having a measurable physical property. The leaving signal group, which preferably exhibits an altered physical property after having been cleaved off, can be a chromophoric, chemiluminescent or fluorescent group whose property can be measured. Preference is given to chromophoric signal groups whose optical property is determined photometrically, such as para-nitroanilide (pNA), whose absorption can be measured at a wavelength of 405 nm after the group has been cleaved off by thrombin. Examples of synthetic thrombin substrates which are suitable for implementing the present invention are described, for example, in claims 1 to 5 in patent specification EP 0 802 986-B1.

The concentration of thrombin substrate is to be adjusted such that the substrate cannot be consumed completely during the course of the reaction so as to ensure that the quantity of released indicator is proportional to the enzymatic activity of the free and $\alpha_2$-macroglobulin-complexed thrombin formed during the course of the coagulation reaction [see Hemker et al. (1993) Thromb. Haemostasis 70: 617-624].

In order to avoid the formation of interfering fibrin clots, either the sample can be defibrinated beforehand using known methods, for example by means of adding snake venoms such as batroxobin, by means of heat, or by means of precipitation or immunoaffinity chromatography, or the sample can be treated with an inhibitor of fibrin polymerization. Peptides which are suitable for inhibiting fibrin polymerization, without inhibiting the thrombin which is present in the sample, are, for example, the subject of claims 1 and 2 in patent specification EP 0 456 152-B1.

In order to induce thrombin formation, it is possible, for example, to use solutions which contain $Ca^{2+}$ ions and, additionally for example, thromboplastin or a contact activator such as kaolin, phospholipids, snake venom or thrombomodulin and activated protein C. In each case depending on the diagnostic question being asked, the skilled person can choose from the large number of known activators of blood coagulation in order to consider either a constituent part, or the whole, of the coagulation system (see also EP 0 420 332-B1).

The physical property of the converted thrombin substrate is preferably measured from the time of the addition of the thrombin formation activator to the sample onwards, preferably at time intervals of from 1 to 25 measurements per 10 seconds. The chronologically assigned measurement values describe the turnover kinetics of the thrombin substrate or the overall reaction kinetics (see also curve A in FIGS. 1 to 3). The slope of the overall reaction curve is a measure of the reaction rate at which the thrombin substrate is cleaved or the signal group (indicator) is released.

Measuring the quantity of indicator which is released over time gives a typical overall reaction curve which can be roughly divided by visual inspection into three phases:
a) a first phase, i.e. what is termed the lag phase, which begins at time $t_0$ with the addition of the thrombin formation activator and is characterized by a shallow curve, that is a low reaction rate. This is the part of the reaction in which thrombin formation gets underway. Depending on the design of the test, the lag phase can last between 0 and 30 minutes.
b) a second phase, i.e. what is termed the exponential phase, which follows the lag phase and is characterized by a steeply rising curve, that is a high reaction rate. This phase comprises the part of the reaction in which the rate of formation of thrombin reaches its maximum and, finally, the rate of inhibition of thrombin is also highest. In this phase, the thrombin substrate is converted both by free thrombin and by the activity of the $\alpha_2$-macroglobulin/thrombin complex ($\alpha_2$MT). This phase lasts until the time at which free thrombin is no longer present.
c) a third phase, i.e. what is termed the saturation phase, which is characterized by a curve which is rising continuously but it more shallow than that of the exponential phase. This phase comprises the part of the reaction in which conversion of the thrombin substrate is to be attributed exclusively to the activity of the $\alpha_2$-macroglobulin/thrombin complex ($\alpha_2$MT). This phase can be recognized by the fact that the reaction rate, or the quantity of indicator released per unit of time, remains constant resulting in the overall reaction kinetics assuming a course which is continuously ascending linearly.

In addition to depending on the endogenous potential of the sample for forming and inhibiting thrombin, the course of the reaction curve, or the duration of the three different reaction phases, also depends on the test-specific reaction conditions which are selected. Examples of these reaction conditions, which the skilled person can vary depending on the diagnostic question and which can have an effect on the conversion kinetics, are the nature and the concentration of the thrombin formation activator employed or the nature and manner of the pretreatment of the sample material. In each case depending on the test design, the overall duration of the reaction has to be determined empirically in routine preliminary experiments in order, in this way, to be able to adapt the duration of the measurement such that sufficient account is taken of all three reaction phases during a measurement. As is evident from the implementation example and FIGS. 1 to 3, an overall reaction duration of 20 minutes is adequate for the determination of the endogenous thrombin potential which is described therein by way of example.

The measurement is continued until the formation and inhibition of the free thrombin in the test assay have come to an end and the measured turnover kinetics of the thrombin substrate is only to be attributed to the activity of the $\alpha_2$-macroglobulin/thrombin complex ($\alpha_2$MT). A particularly preferred measurement duration is characterized by the fact that the phase of the reaction in which conversion of the thrombin substrate is exclusively to be attributed to the activity of the $\alpha_2$-macroglobulin/thrombin complex ($\alpha_2$MT), i.e. the saturation phase, spans a sufficiently large period of time for it to be possible to determine the raw ETP value reliably.

In the method according to the invention, the linear region of the saturation phase of the overall reaction kinetics is first of all determined within a predetermined, test-specific time window.

This time window, whose starting point is also termed $t_{min}$ and whose end point is also termed $t_{end}$ in that which follows, is to be specified such that it reliably excludes the lag phase, since linear regions of the overall reaction kinetics which may possibly arise during the course of the lag phase are to be excluded from the analysis.

The starting point $t_{min}$ is to be specified such that it is located chronologically downstream of the lag phase. The starting point $t_{min}$ is preferably located at the end of the exponential phase or in the region of the transition from the exponential phase to the saturation phase (see also FIG. 1).

The end point $t_{end}$ has then to be specified such that it is located in the saturation phase and the resulting time window $t_{min}$ to $t_{end}$ encompasses at least three measurement points within the saturation phase.

The position and size of the time window are preferably specified such that the time window encompasses more than three measurement points in the saturation phase, particularly preferably from 4 to 500 measurement points, very particularly preferably from 100 to 300 measurement points.

The time window within which the linear region is to be determined is a test-specific parameter which is to be specified in dependence on the selected reaction conditions. To this end, the skilled person can determine the typical course of the reaction curve under constant reaction conditions in a number of routine preliminary experiments. Known samples which exhibit different endogenous thrombin potentials (ETP values in brief) are advantageously to be used for these preliminary experiments so as to ensure that account can be taken of the variability of the reaction phase duration when predetermining the test-specific time window. In this way, the skilled person can define the time window such that it is guaranteed that, when unknown samples are being analyzed, the starting point $t_{min}$ is always located chronologically downstream of the lag phase and the end point $t_{end}$ is specified such that the resulting time window encompasses at least three measurement points in the saturation phase.

The linear region within the predetermined time window is preferably determined using a regression method.

In a particularly preferred embodiment of a regression method, the square of the Pearson's correlation coefficient r:

$$r = \frac{n \circ \sum_{i=1}^{n} t_i \circ K_i - \sum_{i=1}^{n} t_i \circ \sum_{i=1}^{n} K_i}{\sqrt{\left[n \circ \sum_{i=1}^{n} t_i^2 - \left(\sum_{i=1}^{n} t_i\right)^2\right] \circ \left[n \circ \sum_{i=1}^{n} K_i^2 - \left(\sum_{i=1}^{n} K_i\right)^2\right]}} \quad (3)$$

in which n is the number of measurement points in the time window,
i is a numeric counter variable,
$t_i$ is a series containing the time values of the measured reaction kinetics, and
$K_i$ is a series containing the measurement values of the measured reaction kinetics, is formed for each possible time window whose end point corresponds to $t_{end}$ and whose starting point corresponds to $t_{min}$ or an arbitrary measurement point within the predetermined time window $t_{min}$ to $t_{end}$.

The square of the Pearson's correlation coefficient, $r^2$, is a measure of the linearity of the reaction curve in the given measurement value range or time window. $r^2$ can assume values between 0 and 1. The higher the value is, the better is the linearity. The maximum of the squares of the Pearson's correlation coefficients $r_i$, which are calculated in this way, is determined and the time window having the maximum value is selected as the region or the reaction phase having the best linear course. If several time windows exhibit the same maximum value, the largest of these windows is selected.

In another preferred embodiment, it is possible to define a requisite minimum size for the linear region. In order to ensure a particularly reliable determination of the endogenous thrombin potential, the skilled person may specify that the linear region, which is in the end to be used as the basis for determining the endogenous thrombin potential, should not fall below a defined minimum number of measurement points, i.e. a defined minimum size. Since the minimum size of the linear region which is to be used for determining the raw ETP value should be made dependent on the course of the reaction curve or on the scatter of the measurement values in the linear region, the skilled person should specify the minimum range of the test-specific reaction conditions which he has selected such that there is adequate statistical certainty for the determination of a reliable raw ETP value. If the time window with the best linear course does not satisfy the predetermined minimum size, it is then possible, for example, to use, for the subsequent analysis, the region which precisely encompasses the defined minimum number of measurement points and whose end point corresponds to $t_{end}$. The advantage of this approach is that, for example, even kinetics in which individual measurement values deviate markedly ("be outliers") do not have to be completely discarded but can still be analyzed. A raw ETP value which is determined in this way can be issued together with an appropriate comment so as to enable the user, for example, to appraise the reaction curve by visual inspection.

A further feature of the method according to the invention is that the binding constant C of thrombin to $\alpha_2$-macroglobulin is determined iteratively using the slope A of the overall reaction kinetics in the linear region of the saturation phase, which corresponds to the slope of the $\alpha_2$MT kinetics.

This methodological step is based on the fact that the conversion of the thrombin substrate in the saturation phase is due solely to the enzymic activity of the $\alpha_2$MT complex. The rate of the reaction by which the thrombin substrate is cleaved, i.e. the quantity of indicator which is released per unit of time, correlates with the slope of the overall reaction curve. Since the concentration of $\alpha_2$MT complex remains constant in the saturation phase, the same quantity of thrombin substrate is cleaved per unit of time, resulting in the overall reaction curve rising linearly. Consequently, the slope A of the linear region of the overall reaction kinetics K(t) in the saturation phase can be equated with the slope of the $\alpha_2$MT kinetics $\alpha_2$MT(t).

Taking account of the differential equation (2)

$$\frac{\partial [\alpha_2 MT(t)]}{\partial t} = C \circ T(t)$$

it consequently holds that:

$$\frac{\partial K(t)}{\partial t} = \frac{\partial [\alpha_2 MT(t)]}{\partial t} = C \circ T(t) = A \quad (4)$$

The slope A of the overall reaction kinetics K(t) can preferably be calculated using a linear regression:

$$A = \frac{n \circ \sum t_i \circ K_i - (\sum t_i) \circ (\sum K_i)}{n \circ \sum t_i^2 - (\sum t_i)^2} \quad (5)$$

in which n is the number of measurement points in the linear region of the saturation phase, i is a numeric counter variable, $t_i$ is a series containing the time values in the linear region of the saturation phase, and $k_i$ is a series containing the measurement values of the measured overall kinetics in the linear region of the saturation phase.

Since, according to equation (4), C·T(t) is equal to A, it ought, strictly speaking, to hold in the linear region that:

$$C \cdot T(t) - A = 0 \quad (6)$$

Since, however, one is dealing with a series of error-containing thrombin kinetics values $T(t_i)$ which do not form an ideal straight line, this requirement is not met.

For this reason, it is advantageous, instead of equating $C \cdot T(t_i)$ with A, to use a method of compensation calculation to minimize the deviations of the calculated slope of $\alpha_2 MT$, which, according to equation (4), is equal to $C \cdot T(t_i)$, from the slope A by varying C. The use of the method of the least squares, which is also termed the method of the least squares best fit, is particularly advantageous for this purpose.

According to the method of the least squares, it is consequently to be required that:

$$\sum_{i=istart}^{iend} (C \cdot T_i - A)^2 = \text{Min!} \quad (7)$$

in which $t_i = T(t_i)$ is the thrombin kinetics value at time $t_i$, istart is the index of the beginning of the linear region, iend is the index of the end of the linear region.

A necessary condition for satisfying the requirement is that the derivative with respect to C vanish. C is consequently to be determined such that $$\frac{\partial \sum_{i=istart}^{iend} (C \circ T_i - A)^2}{\partial C} = 0 \quad (8)$$

The following is obtained by solving the equation for C:

$$C = A \circ \frac{\sum_{i=istart}^{iend} T_i}{\sum_{i=istart}^{iend} T_i^2} \quad (9)$$

Since the constant C has a circuit feedback to equation (2) because the value of the constant C depends on the thrombin kinetics T, which, because of equation (13), is in turn a function of the constant C, C is determined iteratively by taking the results of an iteration step as the starting values of the next iteration step which in each case follows:

$$C_{j+1} = A \circ \frac{\sum T_i(C_j)}{\sum T_i^2(C_j)} \quad (10)$$

in which $C_0 = 0$ and i is the numeric index for the thrombin kinetics values $T(t_i)$, and j is the numeric index for the iterations.

A termination criterion is defined for the purpose of ending the iteration. The termination criterion is to be specified by the skilled person test-specifically, as a function of the reaction conditions which are selected in a number of routine preliminary experiments, by examining the time from which the calculated thrombin kinetics no longer changes significantly. The termination criterion is preferably defined such that when the deviation $|C_j - C_{j+1}|$ is greater than a predetermined maximum value $\epsilon$, $C_j$ is set equal to $C_{j+1}$ and equation 13 is calculated once again using the new $C_j$ until the deviation $|C_j - C_{j+1}|$ no longer exceeds $\epsilon$.

Another feature of the present method is that the values of the $\alpha_2 MT$ kinetics $\alpha_2 MT(t)$ are determined. The $\alpha_2 MT$ kinetic value $\alpha_2 MT(t)$ can now be determined for each time point using the C binding constants which have been determined. For this, the differential equation (2) is solved numerically taking account of equation (1), and it follows that:

$$\frac{\partial [\alpha_2 MT(t)]}{\partial t} + C \circ \alpha_2 MT(t) = C \circ K(t) \quad (11)$$

Equation (11) is then formulated as a finite difference [in this regard, see also Fritsch, Herbert: Finite-Diffenezen-Methode [Method of finite differences]. IRB Verlag Stuttgart, 1998 (ISBN 3816712797) or Marshal, Dietrich: Finite Differenzen und Elemente. Numerische Lösung von Variationsproblemen und partiellen Differentialgleichungen [Finite differences and elements. Numeric solution of variation problems and partial differential equations]. Springer-Verlag Berlin Heidelberg, 1989 (ISBN 3540501924)]:

$$\frac{\alpha_2 MT_{i+1} - \alpha_2 MT_i}{t_{i+1} - t_i} + C \circ \alpha_2 MT_i = C \circ K_i, \quad (12)$$

from which the time series for the $\alpha_2 MT$ kinetics values can then be generated:

$$\alpha_2 MT_{i+1} = C \circ K_i \circ (t_{i+1}-t_i) - \alpha_2 MT_i \circ (C \circ (t_{i+1}-t_i)-1) \quad (13)$$

in which $\alpha_2 MT_0 = 0$.

Using the C binding constants calculated in equation (10), the measured K kinetics values and the corresponding time values t, the $\alpha_2 MT$ kinetics value $\alpha_2 MT(t)$ can be determined for each time point using equation (13).

A further feature of the method according to the invention is that the values of the $\alpha_2 MT$ kinetics are subtracted from the corresponding values of the overall reaction kinetics. In order to determine the thrombin kinetics value T(t) at the time point i+1, the difference is formed between the overall reaction kinetics value K(t), which is measured at the time point i+1, and the $\alpha_2 MT$ kinetics value $\alpha_2 MT(t)$, which is determined for the preceding time point i:

$$T(t_{i+1}) = K(t_{i+1}) - \alpha_2 MT(t_i) \quad (14)$$

A further feature of the method according to the invention is that the average is formed of the values which were determined for the kinetics of the free thrombin T(t) in the linear region of the saturation phase.

In the linear region of the saturation phase of the overall reaction kinetics, the thrombin kinetics T(t) should run virtually parallel to the time axis, i.e. the calculated thrombin values should consequently be almost constant. The mean of the values of the kinetics of the free thrombin T(t) which were determined for the linear region of the saturation phase of the overall reaction kinetics (istart to iend) can also be termed the raw ETP value (Etpr):

$$Etpr = \frac{\sum_{i=istart}^{iend} T_i}{n}. \quad (15)$$

In a third embodiment, statistical methods can be used to check the quality of the raw ETP value which has been determined, preferably by forming the coefficient of variation CV of the kinetic values of the free thrombin which were used for the averaging:

$$CV = \frac{\sqrt{\frac{n \circ \sum_{i=istart}^{iend} T_i^2 - \left(\sum_{i=istart}^{iend} T_i\right)^2}{n \cdot (n-1)}}}{Etpr} \circ 100\%. \quad (16)$$

The raw ETP value of a sample which has been determined using the method according to the invention has the unit of the measured physical property of the converted thrombin substrate, such as optical density, absorption in [mU] or the like.

In a preferred embodiment, the coagulation status of a patient or of a patient sample can be established by comparing with the raw ETP value of a normal standard sample. Examples of suitable normal standard samples are pools of blood samples or plasma samples from healthy test subjects. Raw ETP values which are higher than a normal standard raw ETP value point to a thrombophilic disposition. Raw ETP values which are lower than a normal standard raw ETP value point to a hemorrhagic disposition. In addition, comparing the raw ETP value of a sample with the raw ETP values of samples of known thrombin or prothrombin concentration makes it possible to quantify the thrombin which is formed in the sample.

The present invention furthermore relates to instruments wherein the method according to the invention for determining the endogenous thrombin potential is implemented and the instruments are able, on the command of an operator, to automatically analyze the recorded measurement data using the method according to the invention. In this connection, the instruments can be instruments such as automatic coagulation analyzers which, in addition to a unit for the electronic data processing, can also possess devices for manipulating samples and reagents and/or devices for measuring physical properties of the samples or test assays.

The present invention also relates to storage media on which the method according to the invention is stored in the form of a computer program. In addition to fixed disks, these media also include interchangeable data carriers such as diskettes, CDs and DVDs.

The exemplary embodiment which is described below serves to illustrate the method according to the invention and is not to be understood as being a limitation.

EXAMPLE

Automatic Determination of the Raw ETP Values of Plasma Samples

A chromogenic test method, as described in EP 0 420 332-B1, was used for determining the raw ETP values of human plasma samples.

135 µl of platelet-poor plasma (PPP) were mixed with 40 µl of buffer (50 mM tris-HCl, pH 7.4) and 40 µl of a solution which contained a para-nitroanilide (pNA)-coupled oligopeptide which is cleaved specifically by thrombin (Pefachrome®TG; Pentapharm Ltd, Switzerland) and an inhibitor of fibrin polymerization (peptide amide H-Gly-Pro-Arg-Pro-Ala-$NH_2$; see EP 0 456 152-B1). After a 7-minute incubation, 15 µl of $CaCl_2$ (250 mM) and 30 µl of Innovin® (reagent composed of recombinant, human tissue factor and a mixture of synthetic phospholipids; Dade Behring Marburg GmbH, Germany) were added, as thrombin formation activator, to the mixture and measurement of the absorption at a wavelength of 405 nm was begun. The absorption was measured at time intervals of from 1 to 2 measurements per second and over a period of 20 minutes. The measured values were recorded continuously in dependence on the time. The overall reaction kinetics which had thus been determined was then used, with the aid of the method according to the invention, to determine the raw ETP value of the sample. For the test-specific conditions which were selected, a time window having the starting point $T_{min}=650$ seconds and the end point $t_{end}=1078$ seconds was predetermined for determining the linear region of the saturation phase of the overall reaction kinetics.

The mixing of the samples with the reagents, the measurement of the absorption and the automatic determination of the raw ETP value took place in an automated manner on a BCS® coagulation analyzer (Dade Behring Marburg GmbH, Germany) on which the method according to the invention was implemented in the form of software.

A normal standard sample (FIG. 1) and two pathological patient samples (FIGS. 2 and 3) were investigated in this way.

FIGURES

Figure 2:
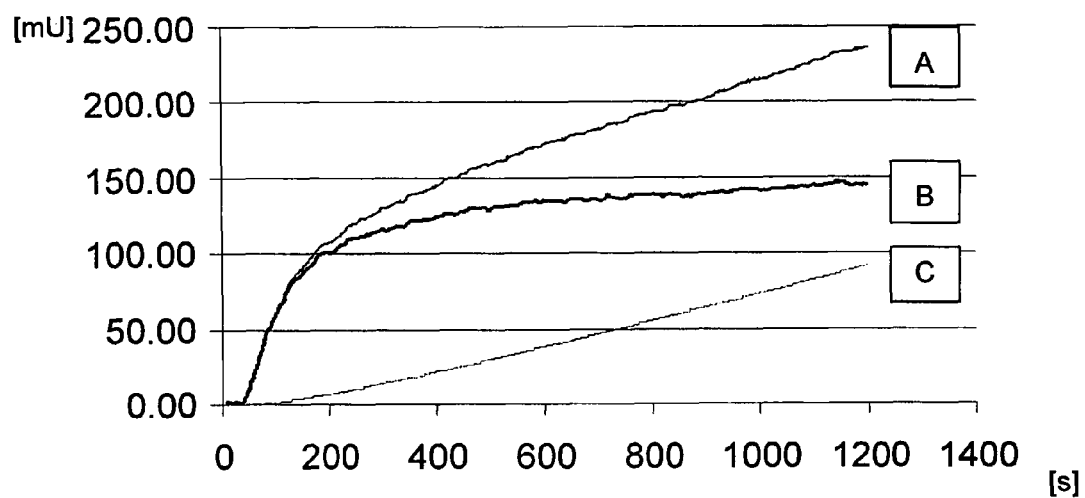
Figure 3:
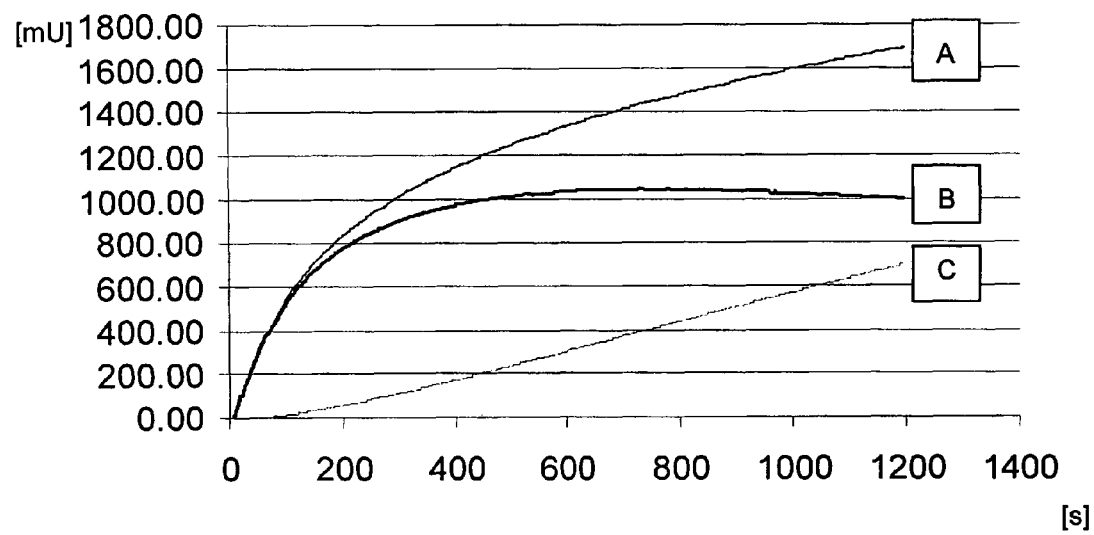
Figure 4:
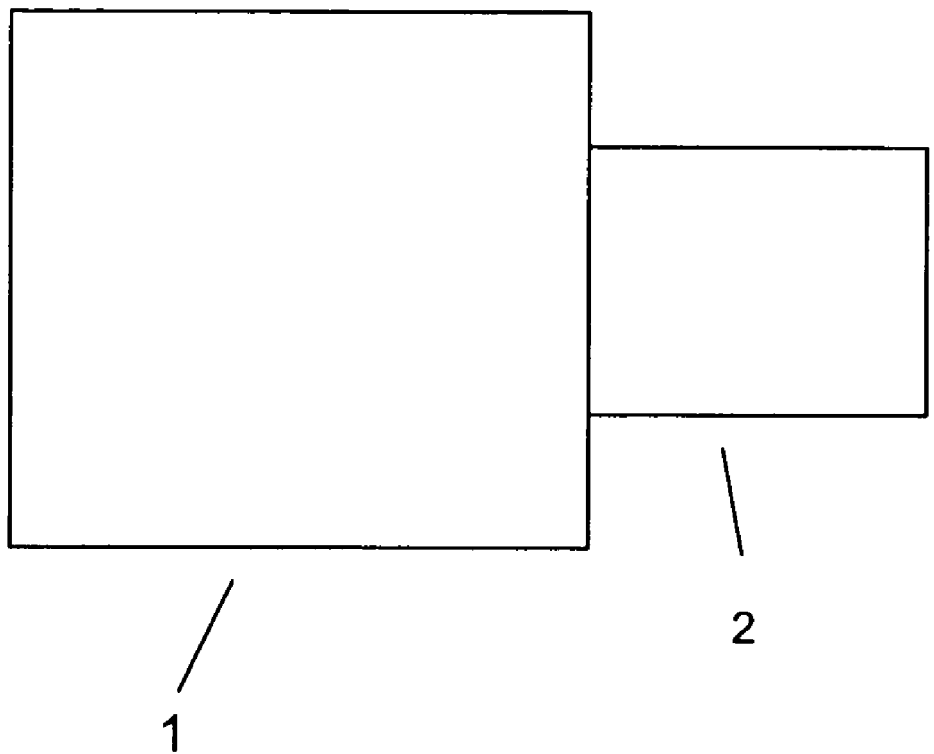

FIGS. 1, 2 and 3 in each case show graphs for the measured overall reaction kinetics K(t) (curve A), i.e. the absorption values [mU] measured in dependence on the time [s], and for the kinetics of the $\alpha_2$MT-macroglobulin/thrombin complex $\alpha_2$MT(t) (curve C) and of the free thrombin T(t) (curve B) which were determined using the method according to the invention.

FIG. 1

Graphic depiction of the measured overall reaction kinetics (A) of a normal plasma sample and of the $\alpha_2$MT and thrombin kinetics which were determined in accordance with the method according to the invention. As an illustration, the approximate durations of the three reaction phases of the overall reaction curve (A) were drawn in, with I denoting lag phase, II denoting exponential phase and III denoting saturation phase. In addition, the test-specific time window $t_{min}$=650 s to $t_{end}$=1078 s which was used here, and within which the region of the overall reaction kinetics K(t) having the best linearity was sought, was drawn in (dotted lines). The linear region (dashed lines) of the overall reaction kinetics was determined to be between the points $i_{start}$=672 s and $i_{end}$=$t_{end}$=1078 s. Within this linear region, the curve (B) for the thrombin kinetics which was determined runs almost parallel to the X axis. A raw ETP value of 378 mU, having a coefficient of variation for the raw value determination of 2.9%, was determined by averaging the thrombin values which were determined within this time window of the linear region.

FIG. 2

Graphic depiction of the measured overall reaction kinetics for a plasma sample from a patient undergoing oral anticoagulation, and of the $\alpha_2$MT and thrombin kinetics which were determined using the method in accordance with the invention. A raw ETP value of 136 mU, which is significantly reduced as compared with the raw ETP value of the normal plasma sample and indicates that the patient has a hemorrhagic coagulation status, was determined by averaging the values, which were determined for the linear region of the overall reaction kinetics, of the kinetics of the free thrombin. The coefficient of variation for the raw value determination is 2.3%.

FIG. 3

Graphic depiction of the measured overall reaction kinetics for a pathological plasma sample, and of the $\alpha_2$MT and thrombin kinetics which were determined using the method according to the invention. A raw ETP value of 1034 mU, which is significantly elevated as compared with the raw ETP value of the normal plasma sample and indicates that the patient has a thrombophilic coagulation status, was determined by averaging the values, which were determined for the linear region of the overall reaction kinetics, of the kinetics of the free thrombin. The coefficient of variation for the raw value determination is 0.7%.

FIG. 4

Diagram showing optional aspects of the invention: an instrument (1) and storage media (2). The storage media may be, for example, fixed disks or interchangeable data carriers such as diskettes, CDs, or DVDs. The storage media may be part of the instrument and contained within the instrument, or it may be attachable to or insertable within the instrument.

The invention claimed is:

1. A method for determining the endogenous thrombin potential (ETP) of a sample of coagulating blood or plasma, comprising
   a) contacting a thrombin substrate with the sample of coagulating blood or plasma,
   b) allowing cleavage of the thrombin substrate to occur,
   c) measuring turnover kinetics of the thrombin substrate as a function of time, wherein the turnover kinetics comprise a saturation phase, and wherein the saturation phase comprises a linear region, and
   d) determining the ETP;

wherein the ETP is determined by:
   i) determining the linear region of the saturation phase of the turnover kinetics within a time window,
   ii) calculating the slope of the linear region of part (i), which slope corresponds to the slope of $\alpha_2$MT kinetics;
   iii) iteratively determining the binding constant of thrombin to $\alpha_2$macroglobulin using slope and kinetics values, wherein the slope consists of said slope of the linear region of the saturation phase;
   iv) determining values of the kinetics of free thrombin by
      (1) determining values of the $\alpha_2$MT kinetics from the binding constant of thrombin to $\alpha_2$macroglobulin, and
      (2) subtracting the values of the $\alpha_2$MT kinetics from the corresponding values of the turnover kinetics; and
   iv) determining the raw ETP value by averaging the values of the kinetics of free thrombin in the linear region of the saturation phase of the turnover kinetics.

2. The method as claimed in claim 1, wherein the time window encompasses at least 3 measurement points within the saturation phase of the turnover kinetics.

3. The method as claimed in claim 1, wherein the linear region of the saturation phase of the turnover kinetics is determined using a regression method.

4. The method as claimed in claim 1, wherein the slope of the linear region of the saturation phase of the turnover kinetics is calculated using a linear regression.

5. The method as claimed in claim 4, further comprising minimizing the deviations of the calculated slope of $\alpha_2$MT from the actual slope of the linear region of the saturation phase of the turnover kinetics.

6. The method as claimed in claim 5, wherein the method of least squares is used to minimize deviations of the calculated slope of $\alpha_2$MT from the actual slope of the linear region of the saturation phase of the turnover kinetics.

7. The method as claimed in claim 1, wherein a time series of the values of the $\alpha_2$MT kinetics is calculated using the method of finite differences.

8. The method as claimed in claim 1, further comprising verifying the quality of the raw ETP value by a method comprising calculating the coefficient of variation of the values of the kinetics of the free thrombin.

9. The method as claimed in claim 1, further comprising comparing the raw ETP value of the sample to the raw ETP value of a normal standard sample.

10. The method as claimed in claim 3, wherein the linear region of the saturation phase of the turnover kinetics is determined by a method comprising obtaining time windows comprising one end point located in the saturation phase of the turnover kinetics and variable starting points located downstream of the lag phase of the turnover kinetics, and calculating the square of the Pearson's correlation coefficient for each said time window.

11. The method as claimed in claim 10, further comprising determining the maximum value from the squares of each said Pearson's correlation coefficient, and selecting the time window corresponding to said maximum value as the linear region of the saturation phase of the turnover kinetics.

12. The method as claimed in claim 11, wherein, if the linear region of the saturation phase of the turnover kinetics falls below a defined minimum width, a window of a previously defined minimum width is selected as the linear region of the saturation phase of the turnover kinetics.

13. The method as claimed in claim 1, wherein the method does not require the input of pre-determined substrate-specific kinetic constants.

14. The method as claimed in claim 1, wherein the method is an automatic method.

15. A method for determining the endogenous thrombin potential (ETP) of a sample of coagulating blood or plasma, comprising
   a) contacting a thrombin substrate with the sample of coagulating blood or plasma,
   b) allowing cleavage of the thrombin substrate to occur,
   c) measuring turnover kinetics of the thrombin substrate as a function of time, wherein the turnover kinetics comprise a saturation phase, and wherein the saturation phase comprises a linear region, and
   d) determining the ETP;
wherein the ETP is determined by:
   i) determining the linear region of the saturation phase of the turnover kinetics within a time window,
   ii) calculating the slope of the linear region of part (i), which slope corresponds to the slope of $\alpha_2$MT kinetics;
   iii) iteratively determining the binding constant of thrombin to $\alpha_2$-macroglobulin using slope and kinetics values, wherein the slope consists of said slope of the linear region of the saturation phase, by the following equation:

$$C_{j+1} = A \cdot \frac{\sum T_i(C_j)}{\sum T_i^2(C_j)}$$

in which $C_0 = 0$, and wherein
C is the binding constant,
A is the slope,
$T_i$ is the thrombin kinetics value at time $t_i$,
i is the numeric index for the thrombin kinetics values $T(t_i)$,
j is the numeric index for the iterations;
   iv) determining values of the kinetics of free thrombin by
      (1) determining values of the $\alpha_2$MT kinetics from the binding constant of thrombin to $\alpha_2$-microglobulin, and
      (2) subtracting the values of the $\alpha_2$MT kinetics from the corresponding values of the turnover kinetics; and
   iv) determining the raw ETP value by averaging the values of the kinetics of free thrombin in the linear region of the saturation phase of the turnover kinetics.

16. The method as claimed in claim 15, wherein the method comprises, in advance of step (iii), selecting kinetics values from within the linear region of the saturation phase from the turnover kinetics of part (c).

* * * * *